US006663874B2

(12) United States Patent
Stevens

(10) Patent No.: US 6,663,874 B2
(45) Date of Patent: Dec. 16, 2003

(54) COMPOSITION TO ALLEVIATE PAIN AND TOPICAL METHOD OF APPLYING SAME

(76) Inventor: Victor Stevens, 2549 E. 5$^{th}$ St., Tucson, AZ (US) 85716

( * ) Notice: Subject to any disclaimer, the term of this patent is extended or adjusted under 35 U.S.C. 154(b) by 84 days.

(21) Appl. No.: 09/766,280

(22) Filed: Jan. 19, 2001

(65) Prior Publication Data

US 2001/0005727 A1 Jun. 28, 2001

Related U.S. Application Data

(63) Continuation-in-part of application No. 09/431,939, filed on Nov. 1, 1999, now abandoned.
(60) Provisional application No. 60/106,688, filed on Nov. 2, 1998.

(51) Int. Cl.$^7$ .............................. A61K 6/00; A61K 7/00; A61K 33/00; A61K 31/34; A61K 31/05
(52) U.S. Cl. ..................... 424/401; 424/725; 424/736; 424/742; 424/744; 424/747; 424/616; 514/474; 514/708; 514/709; 514/714; 514/738; 514/884; 514/858; 514/859; 514/860; 514/861; 514/862; 514/863; 514/864; 514/865; 514/866; 514/867; 514/946; 514/947
(58) Field of Search ................................ 424/703, 616, 424/401, 725, 736, 742, 744, 747; 514/474, 708, 709, 714, 738, 844, 858–865, 886–887, 936, 946–947

(56) References Cited

U.S. PATENT DOCUMENTS

| | | | | |
|---|---|---|---|---|
| 4,227,013 A | | 10/1980 | Haas et al. ................. 560/190 |
| 4,296,104 A | | 10/1981 | Herschler ................... 424/153 |
| 4,296,130 A | | 10/1981 | Herschler ................... 424/337 |
| 4,353,896 A | * | 10/1982 | Levy ........................ 424/195 |
| 4,477,469 A | | 10/1984 | Herschler ................... 424/322 |
| 4,616,039 A | | 10/1986 | Herschler ................... 514/711 |
| 4,847,078 A | * | 7/1989 | Sheppard et al. .............. 424/80 |
| 4,863,748 A | | 9/1989 | Herschler ..................... 426/72 |
| 4,914,135 A | | 4/1990 | Herschler ................... 514/711 |
| 4,973,605 A | | 11/1990 | Herschler ................... 514/708 |
| 5,071,878 A | | 12/1991 | Herschler ................... 514/711 |
| 5,710,141 A | * | 1/1998 | Lin et al. .................... 514/162 |
| 5,811,410 A | | 9/1998 | Falk et al. .................... 514/54 |
| 5,827,834 A | | 10/1998 | Falk et al. .................... 514/54 |
| 5,830,882 A | | 11/1998 | Falk et al. .................... 514/54 |
| 5,852,002 A | | 12/1998 | Falk et al. .................... 514/54 |
| 5,914,319 A | | 6/1999 | Schacht et al. ................ 514/19 |
| 5,929,048 A | | 7/1999 | Falk et al. .................... 514/54 |
| 5,932,560 A | | 8/1999 | Falk et al. .................... 514/54 |
| 5,985,850 A | | 11/1999 | Falk et al. .................... 514/54 |
| 5,985,851 A | | 11/1999 | Falk et al. .................... 514/54 |
| 6,048,844 A | | 4/2000 | Falk et al. .................... 514/54 |
| 6,048,846 A | | 4/2000 | Cochran ..................... 514/168 |
| 6,069,135 A | | 5/2000 | Falk et al. .................... 514/54 |
| 6,117,851 A | | 9/2000 | Sherman et al. ............... 514/62 |

FOREIGN PATENT DOCUMENTS

| | | | |
|---|---|---|---|
| CN | 1083371 A | * | 3/1994 |
| NL | 1000252 C6 | * | 4/1995 |

OTHER PUBLICATIONS

Armine et al., "Essential Oils Used to Control Mites in Honey Bees", Sep., 1996.*
Sneden, Introduction to Natural Products Chemistry, 1995, p77–86.*
Derwent Abstract, NL–1000252C6, Martens et al.*

* cited by examiner

*Primary Examiner*—Russell Travers
(74) *Attorney, Agent, or Firm*—Dale F. Regelman

(57) ABSTRACT

A composition for use by animals, including humans, to alleviate pain and/or inflammation around a painful joint, joint replacement surgery site, muscle, tendon, and/or ligament. A method to ameliorate pain and/or inflammation in or around a joint, muscle, tendon, and/or ligament, by topically applying Applicant's composition.

20 Claims, 2 Drawing Sheets

FIGURE 1

| | Dimethyl-sulfoxide | Dimethyl-sulfone | Hydrogen Peroxide | Ozone | Peracetic Acid | Ascorbic Acid | Glycerin | Glucos-amine | 1st Terpenoid | 2nd Terpenoid | 3rd Terpenoid | 4th Terpenoid |
|---|---|---|---|---|---|---|---|---|---|---|---|---|
| A | 70 | 25 | 2 | | | 1 | | 1 | 0.1 | 0.1 | 0.1 | 0.1 |
| B | 50 | 40 | 10 | | | | | | | | | |
| C | 50 | 45 | 3 | | 2 | | | | | | | |
| D | 55 | 35 | 5 | 5 | | | | | | | | |
| E | 70 | 15 | 2 | | | 2 | 1 | 6 | 0.1 | 0.1 | 0.1 | 0.1 |
| F | 50 | 40 | 5 | | 5 | | | | | | | |
| G | 60 | 27 | 3 | | | 10 | | | | | | |
| H | 70 | 20 | 2 | | 1 | 4 | | 4 | | | | |
| I | 60 | 20 | 3 | 1 | | 6 | 5 | 5 | | | | |
| J | 80 | 10 | 4 | 2 | | 5 | | | | | | |
| K | 80 | 10 | 3 | | | | 5 | 5 | | | | |
| L | 80 | 5 | 6 | | | 4 | 2 | 2 | 1 | 1 | 1 | 1 |
| M | 80 | 6 | 2 | | | 2 | 1 | 1 | 2 | 2 | 1 | 1 |
| N | 90 | 2 | 2 | | | 2 | | | 1 | 1 | 1 | 1 |
| O | 60 | 18 | 2 | | | 8 | | 10 | 0.5 | 0.5 | 0.5 | 0.5 |
| P | 60 | 15 | 7 | | | 6 | | 10 | | | 1.0 | 1.0 |
| Q | 50 | 30 | 1 | | | 7 | | 3 | 4 | 5 | | |

FIGURE 1 (CONT.)

| | | | | | | | | | | | | |
|---|---|---|---|---|---|---|---|---|---|---|---|---|
| R | 75 | 12 | 1 | 1 | 1 | 3 | | | | | | |
| S | 65 | 8 | 3 | | | 9 | | 8 | | | | |
| T | 50 | 10 | 5 | | | 5 | 5 | 0.5 | 5 | 5 | 5 | 5 |
| U | 85 | 10 | 2 | | | 1 | | 2 | | | | |
| V | 70 | 15 | 2 | | 1 | 2 | 3 | 6 | 0.1 | 0.1 | 0.1 | 0.1 |
| W | 70 | 15 | 2 | | | 2 | 1 | 6 | 0.1 | 0.1 | 0.1 | 0.1 |
| X | 70 | 15 | 1 | 1 | | 2 | 1 | 6 | 0.1 | 0.1 | 0.1 | 0.1 |
| Y | 72 | 17 | 3 | | | 2 | | | 1.0 | 1.0 | 1.0 | 1.0 |

COMPOSITION TO ALLEVIATE PAIN AND TOPICAL METHOD OF APPLYING SAME

CROSS REFERENCES TO RELATED APPLICATIONS

This Application is a Continuation In Part of Application having Ser. No. 09/431,939 filed Nov. 1, 1999, now abandoned which claims priority of Provisional Application having Ser. No. 60/106,688 filed Nov. 2, 1998.

FIELD OF THE INVENTION

The instant invention relates generally to topically-applied compositions for providing analgesic and/or anti-inflammatory relief in animal, including humans, and more specifically to compositions containing a first polyol, such as vitamin C, a second polyol, such as glucosamine, a first oxidizing agent, such as hydrogen peroxide, a first polar compound having a dielectric constant greater than about 40, such as dimethylsulfoxide, and a second polar compound having a dielectric constant greater than about 40, such as dimethylsulfone. Applicant's composition further optionally includes a second oxidizing agent and/or one or a plurality of terpenoid compounds. Applicant's invention further relates to a method for topically applying Applicant's composition to animals, including humans.

BACKGROUND OF THE INVENTION

Many patients with localized pain due to arthritis, bursitis, sprain or muscle strain, bruises or hematomas cannot tolerate conventional nonsteroidal anti-inflammatory drugs, commonly known as NSAIDS. In addition, topical administration of conventional NSAIDS has largely been ineffective because only a therapeutically ineffective amount of the drug can penetrate the skin. In addition, indications such as acne, psoriasis and eczema are typically refractory to topical or oral administration of NSAIDS. What is needed is a composition that is effective in treating a wide variety of inflammatory conditions by topical application of the composition. Such a composition In addition, joint pain can often indicate the onset of a condition called osteoarthritis. Osteoarthritis is a degenerative joint disease affecting articular cartilage developing in the fourth and fifth decades of life that was initially believed to be a disease of wear and tear due to mechanical stress on the joints. It is now known that the pathology of osteoarthritis is not entirely mechanical and involves changes in the joint metabolism. Specifically, altered glucosamine metabolism appears to play a key role in the development of osteoarthritis.

An effective treatment of osteoarthritis must address two types of problems: (i) pain, and joint tenderness, swelling and stiffness must be alleviated as an immediate patient's problem; and (ii) the degenerative process must be stopped preferably at its earlier stages. Treatment with anti-rheumatics and nonsteroidal anti-inflammatory drugs has not proven successful. Anti-rheumatics, although quickly effective, were recently shown to impair the very function that physicians were trying to improve, and anti-inflammatory drugs alleviate the pain but do not address the underlying degenerative disorder.

Recent biochemical and pharmacological studies have suggested a novel and more effective treatment of osteoarthritis. These studies have shown that administration of glucosamine tends to normalize cartilage metabolism, inhibiting degradation, and stimulating the synthesis of proteoglycans resulting in partial restoration of the articular function. The therapeutic effectiveness of a treatment with glucosamine has been demonstrated in a number of animal and human studies.

Glucosamine is a building block of the ground substance of the articular cartilage, the proteoglycans. Glucosamine is also the preferential substrate and a stimulant of proteoglycan biosynthesis. Furthermore, glucosamine inhibits the degradation of proteoglycans and rebuilds the experimentally damaged cartilage. Based on these findings, different types of glucosamine were introduced in the therapy of osteoarthritis. The clinical experience with preparations containing glucosamine derivatives confirmed the efficacy and the safety of the glucosamine treatment.

What is needed is a composition for use in animals, including humans, which can alleviate the signs and symptoms of joint pain, including pain related to osteoarthritis, without causing undesirable side effects. What is also required is a convenient method of using such a composition.

SUMMARY OF THE INVENTION

Applicants' invention includes a composition formed by combining a first sulfur-containing compounds having a dielectric constant greater than 40, a second sulfur-containing compound having a dielectric constant greater than 40, and a first oxidizing agent. In other embodiments, Applicant's composition also includes a first polyol, such as vitamin C, in combination with a second polyol, such as glucosamine and/or glucosamine derivatives.

Applicant's invention further includes a method to topically apply Applicant's composition in and around a painful joint, a painful muscle, a painful tendon, and/or a painful ligament. Applicant has found that such topical application of his composition is effective in ameliorating pain resulting from a number of causes including inflammation, arthritis, bursitis, physical injury, joint replacement surgery, muscle/tendon/ligament strains and/or sprains, and the like. Applicant has further discovered that use of the above-recited ingredients in combination a second oxidizing agent and/or in combination with a plurality of terpenoid compounds is especially effective in ameliorating such joint, muscle, tendon, and/or ligament pain in and animals, including humans.

BRIEF DESCRIPTION OF THE DRAWINGS

The invention will be better understood from a reading of the following detailed description taken in conjunction with the drawings in which like reference designators are used to designate like elements, and in which:

FIG. 1 summarizes certain preferred formulations of Applicant's composition.

DETAILED DESCRIPTION OF THE PREFERRED EMBODIMENTS

Applicant's composition includes a first polyol having between 3 and 6 carbon atoms and at least three hydroxyl groups. Naturally-occurring polyols are preferred. For example, Applicant's composition includes embodiments comprising ascorbic acid, compound I, and/or glycerin, compound II. Applicant's first polyol is present in an amount between 0 weight percent and about 10 weight percent.

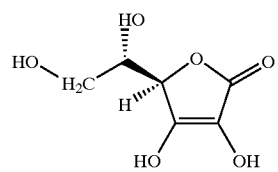

I

-continued

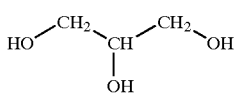

II

Applicant's composition further includes a second polyol having between 3 and 6 carbon atoms and at least three hydroxyl groups. Again, naturally-occurring compounds, and/or their derivatives, are preferred. In certain embodiments, Applicant's composition includes one or more substituted mono-saccharides, having the general structure of compound III.

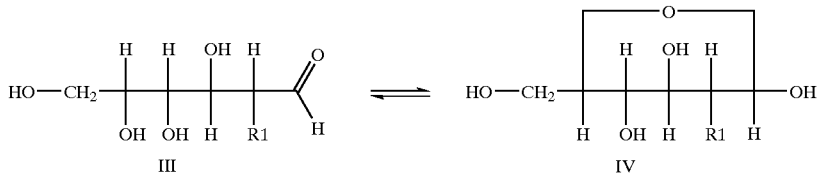

wherein R1 is selected from the group consisting of —OH, —NH$_2$, —NH$_3$$^+$X$^-$, and mixtures thereof, wherein X$^-$ is selected from the group consisting of chloride, bromide, iodide, sulfate, acetate, propionate, benzoate, and mixtures thereof.

Those skilled in the art will appreciate that linear aldehyde III is in equilibrium with cyclic acetal IV. Applicant's second polyol is present in an amount between 0 weight percent and about 10 weight percent.

Applicant's composition further includes a first polar compound containing sulfur and having a dielectric constant greater than having structure V. In one embodiment, Applicant's first polar compound includes one or more materials having structure V:

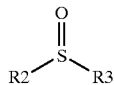

V wherein R2 and R3 are selected from the group consisting of methyl, ethyl, propyl, n-butyl, s-butyl, t-butyl, and mixtures thereof. Applicant's first polar compound is present in an amount between about 50 weight percent and about 90 weight percent.

Applicant's composition further includes a second polar compound containing sulfur, and having a dielectric constant greater than about 40. In one embodiment, Applicant's second polar compound includes one or more materials having structure VI:

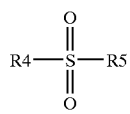

VI wherein R4 and R5 are selected from the group consisting of methyl, ethyl, propyl, n-butyl, s-butyl, t-butyl, and mixtures thereof. Applicant's second polar compound is present in an amount between 0 weight percent and about 40 weight percent.

Applicant's composition further includes a first oxidizing agent. Applicant's first oxidizing agent is selected from the group consisting of hydrogen peroxide, ozone, peracetic acid, and mixtures thereof. Applicant's first oxidizing agent is present in an amount between about 1 weight percent and about 10 weight percent.

In certain embodiments, Applicant's composition includes one or more lipophilic compounds. Applicant has found that inclusion of these lipophilic compounds enhances the transdermal delivery of the total composition, and also ameliorates some of the undesirable side effects resulting from the use of certain skin penetration enhancers, such as dimethylsulfoxide. These undesirable side effects include a "garlicy taste" and malodorous breath.

In general terms, the lipophilic compounds suitable for use herein include terpenoid compounds having between 10 and 15 carbon atoms. These terpenoid components are included at individual levels between 0 weight percent and about 5 weight percent.

The terpenoid components of Applicant's composition include one or more compounds naturally found in, for example, eucalyptus oil, wintergreen oil, oregano oil, bay leaf oil, peppermint oil, spearmint oil, clove oil, sage oil, sassafras oil, lemon oil, orange oil, anise oil, benzaldehyde, bitter almond oil, camphor, cedar leaf oil, marjoram oil, citronella oil, lavendar oil, mustard oil, pine oil, pine needle oil, rosemary oil, thyme oil, cinnamon leaf oil, and mixtures thereof.

Applicant's first terpenoid component includes one or more naturally-occurring cyclic ether compounds having between about 10 and about 15 carbon atoms. Examples of such cyclic ethers include 1,4-cineole, compound VI and 1,8-cineole, compound VII. In certain embodiments, Applicant's composition includes mixtures of compound VI and compound VII.

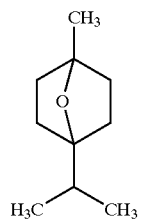

VI

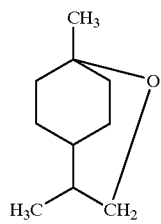

VII

Applicant's second terpenoid component includes one or more compounds having between about 10 carbon atoms and about 15 carbon atoms, wherein those compounds comprise one hydroxyl group. For example, certain embodiments of Applicant's composition include hexahydrothymol, compound VIII.

VIII

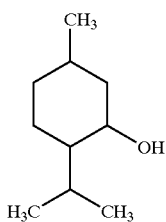

Applicant's third terpenoid component comprises compounds having between about 10 carbon atoms and about 15 carbon atoms, wherein these compounds comprise either a cycloalkene or an alkene moiety. For example, certain embodiments of Applicant's composition include β-pinene, compound IX and/or menthene, compound X.

IX

X

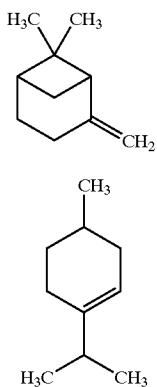

Other embodiments include limonene, α-pinene, citrene, carvene, and the like.

Applicant's fourth terpenoid component comprises fully saturated compounds including a substituted cyclohexane moiety and between about 10 carbon atoms and about 15 carbon atoms. For example, certain embodiments of Applicant's composition include p-menthane, compound XI.

XI

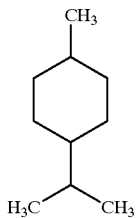

FIG. 1 summarizes preferred embodiments A through X of Applicant's composition. The amounts recited in FIG. 1 are in weight percent. The individual components recited for each embodiment set forth in FIG. 1 can be combined using conventional equipment and techniques. The various ingredients can be combined with one another in any order. In order to assure homogeneity, the combinations set forth in FIG. 1 can be manually agitated or mechanically mixed using, for example, a magnetic stirring apparatus and a magnetic stir bar, an overhead stirring apparatus, and the like.

Applicant's method to treat joint pain includes an embodiment wherein Applicant's composition is incorporated into a carrier, such as a liquid, gel, solid matrix, or pressure sensitive adhesive. In certain embodiment, Applicants' method does not include use of a backing material. In alternative embodiments, Applicant's method includes use of a backing in combination with a carrier. In these embodiments, the portions of the carrier that are not in physical contact with the skin are covered with a backing. The backing serves to protect from the environment the carrier and the components contained in the carrier, including the composition being delivered. Backings suitable for use with Applicants' method include metal foils, metalized plastic films, and single layered and multilayered polymeric films.

In one embodiment, Applicants' method comprises transdermal delivery of Applicant's composition dissolved in a solvent system. The solvent system includes water, and optionally one or more lower alcohols such as ethanol, isopropyl alcohol, propyl alcohol, and the like. Preferably, such alcohols have carbon contents between 2 and about 6. The solvent system may additionally include glycols such as ethylene glycol, propylene glycol, glycerol, and the like.

The solvent system may also include one or more ketones, ethers, and esters. Examples include acetone, methylethylketone, dimethylether, diethylether, dibutylether, and alkyl acetates, alkyl propionates, alkyl butyrates, and the like.

Although solutions of Applicant's composition are preferred, emulsions are also effective. Such emulsions may be aqueous, wherein the aqueous phase is the major and continuous phase, or non-aqueous, wherein a water-insoluble solvent system comprises the continuous phase.

Applicants' transdermal formulation may also contain agents known to accelerate the delivery of medicaments through the skin or mucosa of animals, including humans. These agents are sometimes known as penetration enhancers, accelerants, adjuvants, and sorption promoters, and are collectively referred to herein as "enhancers." Some examples of enhancers include polyhydric alcohols such as dipropylene glycol; oils such as olive oil, squalene, and lanolin; polyethylene glycol ethers and fatty ethers such as cetyl ether and oleyl ether; fatty acid esters such as isopropyl myristate; fatty acid alcohols such as oleyl alcohol; urea and urea derivatives such as allantoin; polar solvents such as dimethyldecylphosphoxide, methyloctylsulfoxide, dimethylacetonide, dimethyllaurylamide, dodecylpyrrolidone, isosorbitol, decylmethylsulfoxide, and dimethylformamide; salicylic acid; benzyl nicotinate; bile salts; higher molecular weight aliphatic surfactants such as lauryl sulfate salts. Other agents include oleic acid and linoleic acids, ascorbic acid, panthenol, butylated hydroxytoluene, tocopherol, tocopheryl acetate, tocopheryl linoleate, propyloleate, isopropyl palmitate, oleamide, polyoxyethylene lauryl ether, polyoxyethylene olelyl ether and polyoxyethylene oleyl ether. In this embodiment, these skin penetration enhancers are present from about 0.01 weight percent to about 5 weight percent.

Applicants' has found that topical application of his composition over a painful joint, and transdermal delivery of that composition tends to minimize injury-produced vascular dilatation and the greatly increased blood flow associated therewith, and/or exudation of fluid from blood vessels into tissues with concomitant swelling, and/or migration of leukocytes into the tissues, and/or gelation of fibrogen in intercellular spaces. When tissue injury occurs, whether caused by bacteria, trauma, chemicals, heat, or any other phenomenon, the body's inflammatory response is stimulated. In response to signals released from the damaged cells (e.g., cytokines), extravascularization of immune effector cells is induced. Under ordinary circumstances these invading immune effector cells kill the infectious agent and/or infected or damaged cells (through the release of killing substances such as superoxides, performs, and other antimicrobial agents stored in granules), remove the dead tissues and organisms (through phagocytosis), release various biological response modifiers that promote rapid healing and covering of the wound (quite often resulting in the formation of fibrotic scar tissue), and then, after the area is successfully healed, exit from the site of the initial insult.

Once the site is perceived to be normal, the local release of inflammatory cytokines ceases and the display of adhesion molecules on the vessel endothelium returns to basal levels. In some cases, however, the zeal of these interacting signals and cellular systems, which are designed to capture and contain very rapidly multiplying infectious agents, act to the detriment of the body, killing additional, otherwise healthy, surrounding tissue.

Applicant's composition can be conveniently topically applied to the area of a painful joint, muscle, tendon, and/or ligament using a device which includes incorporating the composition into an appropriate carrier, and applying that composition/carrier combination to an appropriate backing. For example, a device to transdermally deliver Applicant's composition can be prepared by using the following method; preparing a coating formulation by mixing a solution of the adhesive in a solvent system containing Applicant's composition, and any other desired components, to form a homogeneous solution or suspension; applying the formulation to a substrate such as a backing or a release liner; using well known knife or bar or extrusion die coating methods; drying the coated substrate to remove the solvent; and laminating the exposed surface to a release liner or backing.

In the alternative, Applicant's composition may be applied to the area of a painful joint, muscle, tendon, and/or ligament using a topical spray mechanism, wherein Applicant's composition may, optionally, include an appropriate propellant. Such topical sprays may include aerosol sprays or products containing a propellant. While any of the known propellants may be used in the compositions of this invention, preferred propellants include the non-halogenated hydrocarbons, particularly the lower boiling hydrocarbons such as C3–C6 straight and branched chain hydrocarbons (e.g., propane, butane, and/or isobutane), ethers (e.g., dimethyl ether), hydrofluorocarbons, and compressed gases (e.g., nitrogen and carbon dioxide). In other embodiments, Applicant's composition is applied to the skin using a topical foam rather than a topical spray application.

In another embodiment, Applicant's composition can be added to the water in a tub, spa, Jacuzzi apparatus, and the like. Immersion of an animal, including a human, into that water then results in a whole-body topical application of Applicant's composition.

The following examples are presented to further illustrate to persons skilled in the art how to use Applicant's composition and method. These examples are not intended as limitations, however, upon the scope of Applicant's invention, which is defined only by the appended claims.

EXAMPLE I

An eighty-three (83) year old female had been confined to a wheelchair for over two (2) years. The subject commenced daily topical application of Embodiment Y (FIG. 1) of Applicant's composition over her knees using a spray device. After such daily topical application for six (6) days, the subject's pain and inflammation was ameliorated to the extent she could stand and walk without assistance.

EXAMPLE II

Thirty years after having the cartilage removed from his left knee, a sixty-one (61) year old male commenced daily topical use of Embodiment E (FIG. 1) of Applicant's composition on that left knee. After four (4) months of such daily topical application, the subject's range of motion for that left knee improved from about 50% to about 85%.

EXAMPLE III

A five (5) year old male black Labrador dog injured his left front paw and leg. The animal manifested swelling in the lower left front leg area, and showed obvious discomfort when attempting to walk. After two (2) days of topical application of Embodiment B (FIG. 1) of Applicant's composition, the swelling had significantly subsided and the subject animal was able to walk without any visible impediment or limp.

While the preferred embodiments of the present invention have been illustrated in detail, it should be apparent that modifications and adaptations to those embodiments may occur to one skilled in the art without departing from the scope of the present invention as set forth in the following claims.

I claim:

1. A topical composition formed by combining:

a first oxidizing agent;

a first polar compound having a dielectric constant greater than about 40, wherein said first polar compound comprises at least 50 weight percent of said composition; and a second polar compound having a dielectric constant greater than about 40, wherein said second polar compound comprises more than 20 weight percent of said composition.

2. The composition of claim 1, wherein said first polar compound has the structure

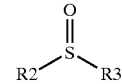

wherein R2 and R3 are selected from the group consisting of methyl, ethyl, propyl, n-butyl, s-butyl, t-butyl, and mixtures thereof.

3. The composition of claim 2, wherein said second polar compound has the structure

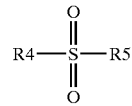

wherein R4 and R5 are selected from the group consisting of methyl, ethyl, propyl, n-butyl, s-butyl, t-butyl, and mixtures thereof.

4. The composition of claim 2, wherein said first oxidizing agent is selected from the group consisting of hydrogen peroxide, ozone, peracetic acid, and mixtures thereof.

5. The composition of claim 1, further comprising:

a first polyol having between three and six carbon atoms and at least three hydroxyl groups; and a second polyol having between three and six carbon atoms and at least three hydroxyl groups.

6. The composition of claim 3, wherein said first polyol is selected from the group consisting of ascorbic acid, glycerol, and mixtures thereof.

7. The composition of claim 6, wherein said second polyol has the structure

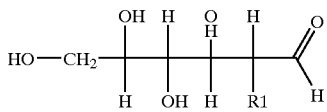

wherein R1 is selected from the group consisting of —OH, —NH$_2$, —NH$_3^+$X$^-$, and mixtures thereof, and wherein X$^-$ is selected from the group consisting of chloride, bromide, iodide, acetate, propionate, benzoate, and mixtures thereof.

8. The composition of claim 7, further comprising a second oxidizing agent.

9. The composition of claim 8, wherein said second oxidizing agent is selected from the group consisting of hydrogen peroxide, ozone, peracetic acid, and mixtures thereof.

10. The composition of claim 6, further comprising a first terpenoid compound.

11. The composition of claim 10, wherein said first terpenoid compound comprises a cyclic ether.

12. The composition of claim 11, wherein said cyclic ether is selected from the group consisting of 1,4-cineole, 1,8-cineole, and mixtures thereof.

13. The composition of claim 10, further comprising a second terpenoid compound.

14. The composition of claim 13, wherein said second terpenoid compound comprises an alcohol.

15. The composition of claim 13, wherein said second terpenoid compound comprises hexahydrothymol.

16. The composition of claim 13, further comprising a third terpenoid compound.

17. The composition of claim 16, wherein said third terpenoid compound comprises an alkene.

18. The composition of claim 17, wherein said alkene is selected from the group consisting of α-pinene, β-pinene, limonene, menthene, citrene, carvene, and mixtures thereof.

19. The composition of claim 16, further comprising a fourth terpenoid compound.

20. The composition of claim 19, wherein said fourth terpenoid compound comprises one or more frilly saturated hydrocarbons having between about 10 carbon atoms and about 15 carbon atoms, and wherein said fourth terpenoid compound further includes a cyclohexyl moiety.

* * * * *